United States Patent
Wheatley et al.

(10) Patent No.: US 7,687,037 B2
(45) Date of Patent: Mar. 30, 2010

(54) AIR FRESHENER AND METHOD

(75) Inventors: Alan J. Wheatley, Draper, UT (US); Christopher D. Anderson, Draper, UT (US)

(73) Assignee: American Covers, Inc., Bluffdale, UT (US)

( * ) Notice: Subject to any disclaimer, the term of this patent is extended or adjusted under 35 U.S.C. 154(b) by 1035 days.

(21) Appl. No.: 11/264,670

(22) Filed: Oct. 31, 2005

(65) Prior Publication Data
US 2006/0196964 A1    Sep. 7, 2006

Related U.S. Application Data (63) Continuation-in-part of application No. 11/050,473, filed on Feb. 2, 2005, now abandoned, and a continuation-in-part of application No. 11/050,463, filed on Feb. 2, 2005, now Pat. No. 7,293,719, which is a continuation-in-part of application No. 10/786,385, filed on Feb. 24, 2004, now Pat. No. 7,137,570.

(60) Provisional application No. 60/451,135, filed on Feb. 28, 2003, provisional application No. 60/517,030, filed on Nov. 3, 2003.

(51) Int. Cl.
*A61L 9/12* (2006.01)
(52) U.S. Cl. ............................. 422/124; 422/123
(58) Field of Classification Search ............... None
See application file for complete search history.

(56) References Cited

U.S. PATENT DOCUMENTS

| | | |
|---|---|---|
| 2,128,118 A | 8/1938 | Burford |
| 2,466,502 A | 4/1949 | Stiller |
| 2,642,248 A | 6/1953 | Semon |
| 3,456,106 A | 7/1969 | Gluschkin |
| 3,654,047 A | 4/1972 | Berkowitz |
| 3,655,129 A | 4/1972 | Seiner |
| 3,948,445 A | 4/1976 | Andeweg |

(Continued)

FOREIGN PATENT DOCUMENTS

| | | |
|---|---|---|
| EP | 0 348 970 | 1/1990 |
| EP | 1 346 734 | 9/2003 |
| WO | WO 00/24434 | 5/2000 |
| WO | WO 00/64498 | 11/2000 |
| WO | WO 02/38029 | 5/2002 |

OTHER PUBLICATIONS

Crown Products 2002 (www.crownprod.com).
FNN-Fleet NewsNet: Company car fleet management solutions pp. 1-4, Roadtest (www.fleetnewsnet.co.uk).
General Electric "Friction Pad Kit" Instructions Field Made for MPD, MPD Friction Pad, Aug. 19, 1988.

*Primary Examiner*—Elizabeth L McKane
(74) *Attorney, Agent, or Firm*—Thorpe North & Western LLP (57) ABSTRACT

An air freshener device includes a scent material interspersed within a polymer body or a polymer gel, and capable of dispersing out of the polymer gel. The polymer body and a polymer gel can be flexible and compressible, and also resilient and returnable to its original configuration. In addition, the polymer body and the polymer gel can have a freestanding, self-supported, three-dimensional shape. The air freshener can be light transmissive in at least a translucent manner, and can have indicia visible therethrough. In addition, the air freshener can have a light source capable of emitting light visible through the body. A vehicle accessory power plug can be coupled to the light source, and sized and shaped to be inserted into a vehicle accessory power socket.

12 Claims, 8 Drawing Sheets

U.S. PATENT DOCUMENTS

| | | |
|---|---|---|
| 3,971,858 A | 7/1976 | Collier et al. |
| 4,184,099 A | 1/1980 | Lindauer et al. |
| 4,226,944 A * | 10/1980 | Stone et al. ............... 512/4 |
| 4,517,326 A | 5/1985 | Cordts et al. |
| 4,594,380 A | 6/1986 | Chapin et al. |
| 4,638,057 A | 1/1987 | Takahashi et al. |
| 4,649,046 A | 3/1987 | Kross |
| 4,703,070 A | 10/1987 | Locko et al. |
| 4,749,222 A | 6/1988 | Idland |
| RE32,834 E * | 1/1989 | Cordts et al. ............ 524/310 |
| 4,874,129 A | 10/1989 | DiSapio et al. |
| 4,880,690 A | 11/1989 | Szycher et al. |
| 4,944,311 A | 7/1990 | Eldridge, Jr. et al. |
| 5,008,115 A | 4/1991 | Lee et al. |
| 5,019,434 A | 5/1991 | Matsumoto |
| 5,036,866 A | 8/1991 | Eldrige, Jr. et al. |
| 5,071,704 A | 12/1991 | Fischel-Ghodsian |
| 5,358,094 A | 10/1994 | Molinaro |
| 5,638,249 A | 6/1997 | Rubino |
| D390,941 S | 2/1998 | Cessaroni et al. |
| 5,762,549 A | 6/1998 | Scheuer et al. |
| 5,780,527 A | 7/1998 | O'leary |
| 5,820,791 A | 10/1998 | Canale |
| 5,845,847 A | 12/1998 | Martin et al. |
| 5,861,128 A | 1/1999 | Vick et al. |
| D404,957 S | 2/1999 | Cheris et al. |
| 5,871,765 A | 2/1999 | Johnson et al. |
| 6,044,202 A | 3/2000 | Junkel |
| 6,111,055 A | 8/2000 | Berger et al. |
| 6,123,906 A * | 9/2000 | Farmer ............... 422/124 |
| 6,190,607 B1 * | 2/2001 | Farmer ............... 422/5 |
| 6,191,197 B1 | 2/2001 | Wang et al. |
| 6,264,887 B1 | 7/2001 | Farmer |
| 6,291,371 B1 | 9/2001 | Shefer et al. |
| 6,309,715 B1 | 10/2001 | Lindauer et al. |
| 6,374,044 B1 | 4/2002 | Freidel |
| 6,375,966 B1 | 4/2002 | Maleeny et al. |
| 6,379,689 B1 | 4/2002 | Aguadisch |
| 6,416,043 B1 | 7/2002 | Eisenbraun |
| D485,343 S | 1/2004 | Wu |
| 6,673,409 B1 | 1/2004 | Wheatley |
| 7,159,792 B2 | 1/2007 | Wheatley et al. |
| 2003/0097936 A1 | 5/2003 | Maleeny et al. |
| 2003/0199421 A1 | 10/2003 | Copfer |

* cited by examiner

AIR FRESHENER AND METHOD

This is a continuation-in-part application of U.S. patent application Ser. No. 11/050,473, filed Feb. 2, 2005 now abandoned, and Ser. No. 11/050,463, filed Feb. 2, 2005 now U.S. Pat. No. 7,293,719; both of which are continuation-in-part applications of U.S. patent application Ser. No. 10/786,385, filed Feb. 24, 2004 now U.S. Pat. No. 7,137,570, which claims the benefit of U.S. Provisional Application Ser. Nos. 60/451,135, filed Feb. 28, 2003, and 60/517,030, filed Nov. 3, 2003; all of which are herein incorporated by reference.

BACKGROUND OF THE INVENTION

1. Field of the Invention

The present invention relates generally to air fresheners and the like.

2. Related Art

Air fresheners are common devices used to improve and/or change the olfactory characteristics of an environment. Such environments can include bathrooms or wash closets, vehicles, lockers, drawers, etc. Such air fresheners typically include a scent that is aesthetically pleasing, such as flowers, fruits, etc.

One common type of air freshener is a two-dimensional, paper-fiber card with a fragrance surrounded in a clear plastic envelope. The envelope is pierced to form an opening, and a portion of the freshener protrudes through the opening to release a scent. The air freshener includes a string or elastic forming a loop to suspend the air freshener. Such air fresheners are commonly utilized in vehicles. One disadvantage with such air fresheners is that the card is moist, and can leak or leach, leaving a stain on other surfaces, such as dashboards. The plastic envelope and the suspending loop act to resist contact between the card, and other surfaces. Another disadvantage with such air fresheners is that they are aesthetically displeasing. Another disadvantage with such air fresheners is that they have a more pronounced and immediate scent release, releasing a majority of the scent in the first few days of use.

Another common type of air freshener has a disc-shaped shell or canister with a scented disc or gel inside. The shell can include an adhesive strip to stick or adhere the shell to a surface. One disadvantage with such air fresheners is that removal of the shell often leaves a residue of the adhesive on the surface, which is aesthetically displeasing. In addition, the scented material can leak and harm the surface.

Some disadvantages of common air fresheners include 1) rapid scent loss or lack of longevity; 2) non-linear or inconsistent scent release over time; and 3) risk of staining. Some air fresheners disperse their scent too rapidly, thus losing effectiveness over time, and not lasting as long as desired. Some air fresheners quickly or rapidly disperse their scent after activation, and then slowly release scent, or release little scent, thereafter. Some air fresheners include materials that can leak and stain.

Another disadvantage with some air fresheners is that they include a non-solid and non-liquid material, or a jelly-like material, that must be contained in some type of container because the jelly is flowable. The material can become dried and cracked over time, presenting an aesthetically displeasing appearance. Again, the scented material can leak and damage surfaces.

SUMMARY OF THE INVENTION

It has been recognized that it would be advantageous to develop an air freshener that is more aesthetically pleasing. In addition, it has been recognized that it would be advantageous to develop an air freshener that is easily located or positioned without marring or otherwise damaging other surfaces. In addition, it has been recognized that it would be advantageous to develop an air freshener that can last for a desired length of time, such as 30 days, and that can have a more constant scent release. In addition, it has been recognized that it would be advantageous to develop an air freshener capable of illuminating.

The invention provides an air freshener device with a vehicle accessory power plug sized and shaped to be inserted into a vehicle accessory power socket. A light source capable of emitting light is coupled to the vehicle accessory power plug. A coherent elastomeric polymer body is disposed adjacent the light source. A scent material is interspersed within the body, and is capable of diffusing out of the body to surrounding air. The body is light transmissive in at least a translucent manner so that the light from the light source being visible through the body In addition, the invention provides an air freshener device includes a head with indicia. A vent rod is coupled to the head and sized and shaped to be inserted into a vehicle air vent. A coherent elastomeric polymer body is coupled to the vent rod, and insertable into the vehicle air vent with the vent rod. A scent material is interspersed within the body, and is capable of diffusing out of the body to surrounding air.

Furthermore, the invention provides a method for providing a desired fragrance. A tacky attachment surface of a pad of an air freshener is secured to a window by specific or mechanical adhesion. The air freshener includes a scent material carried by and dispersable through a coherent, elastomeric polymer body that is light transmissive in at least a translucent manner. The pad is selectively removed from the window.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 23b is a partial exploded view of the air freshener of FIG. 23a;

FIG. 23c is a partial perspective view of the air freshener of FIG. 23a;

FIG. 24b is a cross-sectional side view of the air freshener of FIG. 24a;

FIG. 25 is an exploded side view of another air freshener in accordance with an embodiment of the present invention;

FIG. 26 is an exploded side view of another air freshener in accordance with an embodiment of the present invention;

FIG. 27a is an exploded side view of another air freshener in accordance with an embodiment of the present invention;

FIG. 27b is a side view of the air freshener of FIG. 27a;

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1-5, an air freshener or scent device, indicated generally at 10, in accordance with the present invention is shown for providing a desired and/or aesthetically pleasing scent, fragrance, aroma or neutralizing agent. Air fresheners are one example of a field that can benefit from the present invention. The air freshener 10 can be used in bathrooms, wash closets, vehicles, offices, bedrooms, etc. The desired scent can include, for example, floral, fruit, vanilla, berry, pine, etc. In accordance with one aspect of the present invention, the air freshener 10 can include a flexible and resilient polymer body, such as a polymer gel. The polymer body can be elastic and coherent. Thus, the polymer body can be compressible under an applied force, and substantially returnable to an original configuration upon removal of the applied force. It has been found that the polymer gel provides desired characteristics of aesthetics, flexibility, longevity, substantially constant scent release, and containment. In accordance with another aspect of the present invention, the polymer gel can have a freestanding, self-supported, three-dimensional shape that does not significantly change as the scent is released. In accordance with another aspect of the invention, the air freshener 10 can grip or cling to a surface 14, without mechanical fasteners or additional chemical adhesives. As such, adhesion between the air freshener and the surface is primarily by mechanical and/or specific adhesion. The surface 14 can include windshields, dashboards, computer monitors, glass windows, mirrors, etc.

Figure 1:
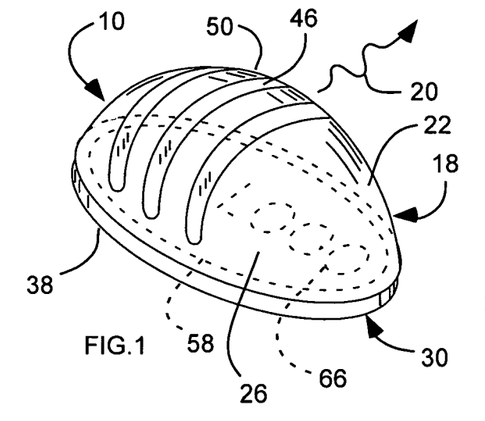
FIG. 1 is a perspective view of an air freshener in accordance with an embodiment of the present invention.
Figure 2:
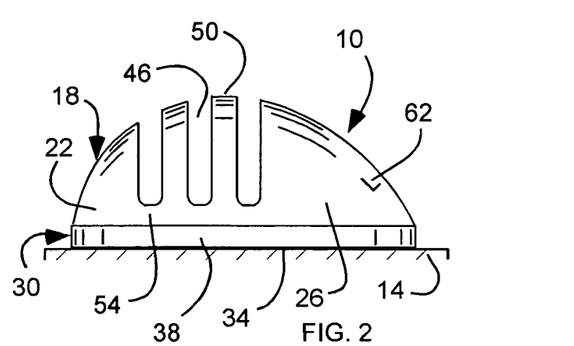
FIG. 2 is a side view of the air freshener of FIG. 1.
Figure 3:
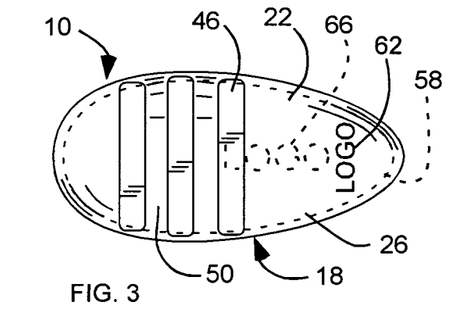
FIG. 3 is a top view of the air freshener of FIG. 1.

The air freshener 10 includes a scent portion 18 for providing the desired scent, indicated by arrow 20. The scent portion 18 can include a carrier material 22 with a scent material of the desired scent interspersed therein. The term "scent material" is used broadly herein to refer to a material that has a scent that can be discernable or smelled, or even a neutralizing agent. Thus, the scent can be an ascertainable smell used to cover other scents, or a neutral agent that eliminates odors or provides a fresher atmosphere. The scent material disperses or diffuses out of the carrier material 22 into the air or atmosphere where it can be detected, or where it can provide a discernable scent. It is believed that the scent material migrates or diffuses through and out of the carrier material or gel. The scent material can be high in volatile notes, or has high volatility and can vaporize or evaporate at low temperatures. The scent material can include a scented oil. For example, suitable scent material can include pine, berry, vanilla, apple, coconut, cherry, pina colada, etc.

The scent portion 18 and/or the carrier material 22 can include a polymer material, such as a polymer gel 26, forming a polymer body. The polymer body and/or polymer gel 26 can be elastic and coherent. Thus, the polymer body can elastically deform under normal conditions. The polymer body can be flexible and resilient, such that the body or gel can compress under an applied force (42 in FIG. 5), but can substantially return to its original configuration upon removal of the applied force. The polymer gel 26, or the polymer body, can have a freestanding, self-supported, three-dimensional shape. Thus, the polymer gel or polymer body can be consistent or solid enough to support or maintain its shape in a freestanding manner without a container. The three-dimensional shape can be any desired shape. The polymer gel 26 can be considered a solid material that is elastic and coherent, and thus flexible and capable of being deformed, but without being flowable. Thus, the polymer gel 26 may have a sufficiently high molecular weight, and/or a sufficiently high viscosity, so that it is a non-flowable gel. In addition, the polymer gel 26 can be considered as stable. Thus, the polymer gel can be bendable, but otherwise substantially maintains its form. The polymer body or polymer gel can be characterized as a polymeric material in the glass state with substantially no macroscopic flow. The polymeric material can have a glass transition temperature greater than approximately 110° F. The polymer gel 26 can retain its gel-like characteristic over time, without drying or cracking, and without becoming hard or brittle.

In one embodiment, the polymer gel 26 can include a polyurethane material or can be a polyurethane gel. The gel can be formed by combining a polyurethane material with a scented oil. Surprisingly, it has been found that such a combination provides a desired scent, but without staining or substantially leaking onto a surface. In addition, the scent portion 18 does not undergo a visually ascertainable physical change, such as drying out or cracking. Thus, the scented portion remains aesthetically pleasing.

In some embodiments, a scented oil and a polymerizable monomer can be combined, along with optional initators or other reactants. Isocyanate reaction polymers have shown good results in connection with the present invention. For example, the polymer gel and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel 26 can include silicone, diffused polyurethane, polyvinylchloride (PVC), ethylene vinyl acetate (EVA), thermoplastic polyurethane (TPU), a polymer encapsulation fragrance delivery platform (Poly-IFF®), thermoplastic elastomer (TPE), polypropylene, ethylene/methacrylic acid (E/MAA) copolymer, in which the MAA groups have been partially neutralized with lithium ions (Surlyn® Dupont), etc.

As a general guideline, the polymer gel 26 can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

As used herein, "elastomeric polymer" and "elastomer" may be used interchangeably and refer to a polymeric material which can be mechanically deformed and upon release returns to an original shape. A coherent elastomer is also non-flowable at or near room temperatures. Further, "cling" and "clingy" refer to a property of a polymeric material which imparts adhesion to most surfaces without a loss of coherency in the polymer. Typically, removal of an elastomeric polymer body with a clingy attachment surface from a substrate does not result in substantial deformation, including temporary deformation, during flexing of the elastomer and/or attachment surface. A clingy attachment surface can be provided directly by the polymer body or can be provided in a separate layer as discussed in more detail herein. Adhesion can occur via mechanical adhesion or specific adhesion. Specific adhesion refers to adhesion dominated, or entirely characterized, by secondary intermolecular forces, i.e. non-covalent bonds, although some covalent bonds can be formed.

Although the polymer gel 26 is freestanding and self-supporting, it is also flexible and resilient. Thus, the scent portion 18 and carrier material 22 can form a flexible and resilient structure or body that can be selectively deformed and can return substantially to the three-dimensional shape. In addition, the carrier material 22 and polymer gel 26 can be light transmissive in at least a translucent manner, as described in greater detail below.

Figure 4:
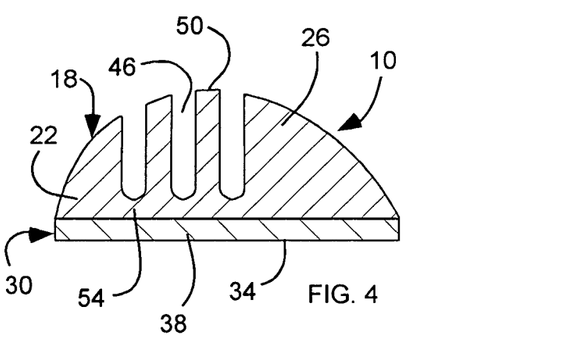
FIG. 4 is a cross-sectional view of the air freshener of FIG. 1.

The air freshener 10 can also include an attachment portion, grip portion or base 30, disposed between the scent portion 18 and the surface 14. Thus, the attachment portion 30 can act as a barrier between the scent portion 18 and the surface 14 to resist potential contact of the scent material with the surface and protect the surface. The air freshener 10 or attachment portion 30 has a lower surface 34 that is disposed on and grips the surface 14. The lower surface 34 can be "tacky," such that the air freshener 10 or lower surface 34 tends to cling to the surface 14 in a frictional fashion, as opposed to a chemical or adhesive manner, and without using mechanical fasteners. The lower surface 34 can be flat, or substantially flat, to provide a greater surface area to cling to the surface 14. Alternatively, the lower surface 34 can be contoured, or can include indentations, to reduce the surface area to facilitate removal of the device from the surface 14.

The attachment portion 30 can include a pad 38 that can be formed of, or can include, a material that provides a "clingy," "tacky" or frictional quality. For example, the pad 38 can include a molded polyurethane material. It has been found that the polyurethane material provides a clingy or tacky quality that remains disposed on the surface. In addition, it has been found that such a polyurethane material typically can be disposed on the surface 14 without marring or otherwise chemically interfering with the material of many surfaces, such as vehicle dashboards. It will be appreciated that many surfaces, such as a vehicle dashboard, have a finished surface configured to be aesthetically pleasing and luxurious. Such surfaces can be formed of a plastic or leather material, and can be expensive to replace or repair. In addition, it will be appreciated that some surfaces are subjected to extreme conditions, such as heat and sunlight. It has been found that the polyurethane material typically clings to the surface 14 without chemically interacting with the material of the surface, or otherwise damage the surface. The polyurethane material of the attachment portion 30 forms a temporary non-chemical bond with the surface 14. The air freshener 10 or attachment portion 30 can be removed from the surface 14 without leaving behind any residue and without damaging the air freshener 10. In this manner, the air freshener 10 can be easily moved to any location the user desires. Because the air freshener or pad includes a polyurethane material, it can be easily cleaned with soap and water, and still retain its tackiness, and is thus reusable. The scent portion 18 can be formed or disposed on the pad 38 or attachment portion 30, and can extend therefrom.

The attachment portion 30 allows the air freshener 10 to be positioned in a desired location, and even re-positioned as desired. For example, the air freshener 10 can be re-positioned to be in sunlight, near a vent, or at an elevated location to facilitate or optimize scent release. Placing the gel in the sunlight can heat the gel, and is believed to increase scent release. Airflow from a vent can carry the scent throughout an area, and can also increase scent release. It is believed that the fragrance or scent can be heavier than air. Thus, positioning the air freshener at an elevated position increases the travel and dispersing of the scent. The air freshener can be positioned so that it avoids contact with other objects, such as clothes in a locker, to avoid staining. In addition, the air freshener can be positioned in a safe location in a vehicle, so that it does not block a driver's view.

The scent and attachment portions 18 and 30, or the carrier material 22 and the pad 38, can form a flexible and resilient structure that can be selectively deformed, and can return substantially to its original shape or configuration. It is believed that selectively squeezing the carrier material can temporarily cause a greater amount of scent to disperse. Thus, a user can selectively deform the carrier material when a greater scent is desired, indicated by arrow 42 in FIG. 5.

The shape and size of the scent portion 18 can be configured to determine the amount or quantity of scent released. For example, the scent portion 18 can have a shape to maximize or control the surface area through which the scent can permeate. The scent portion 18 can be bulbous, semi-bulbous, semi-spherical, tear-drop, oval, oblong, etc. Thus, the attachment portion 30 can have a shape or profile to match the shape of the scent portion. In addition, the material and amount of the scent and the scent portion can be varied to determine the release of the scent. It will be appreciated that the shape or design of the scent portion can vary. For example, the air freshener or scent portion thereof may be shaped to resemble an animal, a flower, a star, a face, a gecko, etc. In addition, the air freshener can include means for increasing the surface area of the scent portion or carrier material, including for example, slots, gaps, grooves, indentations, divots, protrusions, fins, ribs, etc. For example, a plurality of alternating slots 46 and fins or ribs 50 can be formed in the scent portion 18, carrier material 22 or polymer gel. The slots 46 can extend into the carrier material and/or the ribs or fins 50 can extend therefrom.

The slots 46 can be sized so that they terminate before the pad 38, so that there is a portion 54 of the scent portion that remains continuous. It has been found that having the scent portion be a continuous structure resists the fins 50 from tearing away. The bottom of the slots can be curved to reduce stress concentrations and resist tearing.

Figure 15:
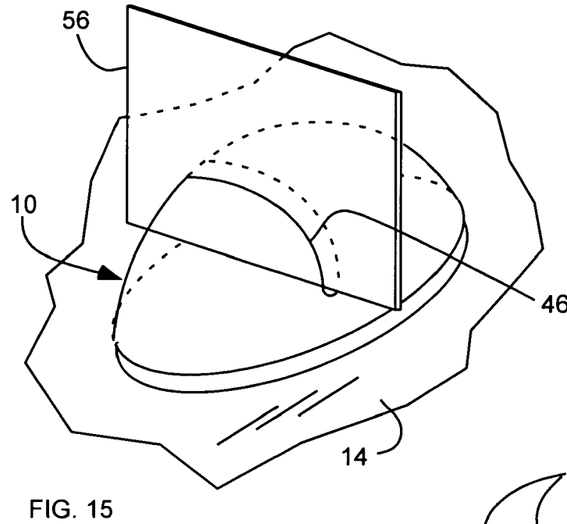
FIG. 15 is a perspective view of the air freshener of FIG. 1.

The slots 46 can be used to receive an article or item, and to hold the article or item 56, as shown in FIG. 15. For example, the article or item can include a note, a business card, directions, etc. Thus, the scent device can be used to hold directions while driving. Alternatively, the scent device can be shaped and configured to hold other items, such as the bridge of eyeglasses or sunglasses, compact discs (CDs), etc.

A barrier 58 can be disposed between the scent and attachment portions 18 and 30, or the carrier material 22 and the pad 38. The barrier 58 can be a layer of material that is heat and oil resistant, such as a nylon, TPU, polyester, or polypropylene sheet, or other synthetic material. The barrier 58 resists migration, leaking or leaching of the scent material or scented oil into the pad 38, and thus to the surface 14. Thus, attachment portion 30 or pad 38, and the barrier 58, act to resist any staining of the surface 14 resulting from scented oil leaking therethrough. It has been found, however, that the scented oil surprisingly does not leak from the scent portion and/or cause stains. It is believed, however, that the polyurethane material of the attachment portion 30 or pad 38 may be susceptible to leaching depending on the scent oil used. Thus, the barrier 58 is intended to resist such leaching. The barrier 58 can be smaller than the attachment portion 30 and scent portion 18 in order to leave a perimeter attachment portion 25 extending around a perimeter thereof so that the scent portion 18 can attach directly to the attachment portion 30.

Figure 5:
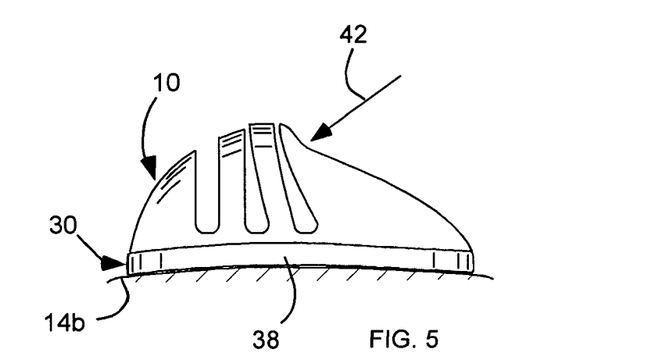
FIG. 5 is a side view of the air freshener of FIG. 1 shown disposed on a curved surface and being compressed by a force.

The air freshener 10, including the attachment portion 30 or pad 38, can be flexible and capable of bending to conform to curves or details in a curved surface 14b, as shown in FIG. 5. The attachment portion 30 or pad 38 also can have a planer configuration and can be used on planar surfaces. The air freshener 10 can be provided with a backing or release layer that prevents or resists the pad 38 from sticking or clinging to any wrapper or packaging of the air freshener. The release layer can include indicia thereon, such as instructions for use and care of the air freshener. The release layer can protrude beyond a perimeter of the pad 38, such as with a tab, to facilitate removal of the release layer from the air freshener. A removable wrapper can be formed around the air freshener to protect the air freshener prior to use. The wrapper and backing layer can be removed prior to placing the air freshener on the surface.

The air freshener 10 can include indicia 62 (FIG. 2) disposed on an outer surface of the air freshener 10 or scent portion 18. The indicia 62 can include artwork, a logo, an advertisement, an instruction, a brand, a trademark, etc. The indicia 62 can be formed by printing on the outer surface, molded into the material of the outer surface, etc.

As described above, the air freshener 10, scent portion 18 or gel can be light transmissive in at least a transparent manner. Thus, the scent portion or gel can be transparent or translucent. Indicia 66 (FIG. 1) can be disposed beneath or behind the scent portion 18, and visible therethrough. Thus, the scent portion 18 can protect the indicia 66 from wear. In addition, the use of a translucent or transparent gel material and the shape of the scent portion can provide a unique visual appearance. Again, the indicia can be a logo, an advertisement, an instruction, a brand, a trademark, etc.

A light color can be disposed behind the scent portion 18 or carrier material 22 to cause the translucent or transparent material to have a luminescent or brighter appearance. For example, the barrier 58 can have a light color, such as white.

The air freshener 10 can be utilized as a promotional device to promote products or services. For example, the indicia 62 and/or 66 can include a logo or trademark for a product, service, business, etc. A method for utilizing the air freshener and/or for promoting includes providing such an air freshener with indicia on or in the air freshener that is indicative of the promotion. Such an air freshener 10 can be given away as a promotional item. A user can then install the air freshener 10, such as in his or her car, thus positioning the indicia in a location where it will be frequently visible.

A method of using the air freshener 10 described above includes removing the air freshener 10 from any wrapping, and/or removing any backing layer from the pad. The air freshener 10 can be attached to a surface 14 by placing the pad 38 against the surface so that the pad clings to the surface. The surface 14 can be any desired surface, such as an interior surface of an automotive window, an automotive dashboard, a bathroom mirror, etc. The scent from the scent portion 18 or polymer gel can disperse or permeate from the scent portion or polymer gel. The air freshener 10 can be disposed in a location subject to heat and/or sunlight, such as an automotive windshield or dashboard. The heat from the sunlight or a heat vent can facilitate the release of scent from the scent device. In addition, airflow from the heat or vent can assist in dispersing the scent. In addition, the air freshener 10 or polymer gel of the scent portion 18 can be flexible and can be pressed, causing the scent portion or gel to deform and to release scent. The pressure can cause the scent to mix and move to the surface of the scent portion.

Figure 6:
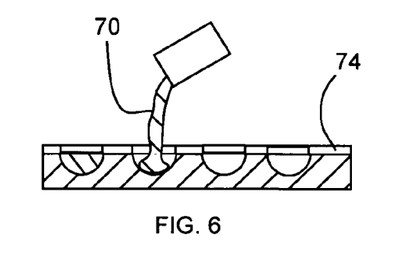
FIGS. 6 and 7 are schematic views of a method for making the air freshener of FIG. 1.
Figure 7:
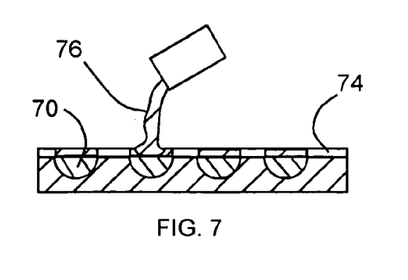

Referring to FIGS. 6 and 7, a method for providing an air freshener is shown. The method includes combining a scent material with a polymer body, such as a polymer gel. The polymer material or polyurethane can be combined with a scented oil. In some embodiments, the scented oil can cause the polymer material to gel. For example, the polymer body or polymer gel can be a polymerization product of the scented oil, polyether polyol, and diphenylmethane diisocyanate (MDI) prepolymer, although other polymerization reactants can also be used. The scented oil can be combined with the polyether polyol. The diphenylmethane diisocyanate (MDI) prepolymer can be combined with the polyether polyol and scented oil to form the polymer gel. For example, a pine scented oil can be combined with a polyether polyol so that the polyether polyol has approximately 40% pine scented oil content. The polyether polyol (with the 40% pine scented oil content) can be added to the diphenylmethane diisocyanate (MDI) prepolymer on a 2:1 ratio, or 2 parts polyol to 1 part prepolymer.

The polymer gel is configured into a desired shape. For example, a material 70 of the scent portion 18, such as the polymer gel, can be poured in a mold 74 with cavities formed in a desired shape. In addition, the air freshener can also be provided with a pad. A material 76 of the pad 38 can be poured in over the material of the scent portion. Pouring one material onto the other can cause the two materials to bond or adhere to one another. Alternatively, the two portions can be separately molded and attached with adhesive. The barrier can be positioned prior to pouring one material onto the other. In addition, the device, or portions thereof, can be made by injection molding.

It will be appreciated that the air freshener 10 can be configured or shaped to appear as various different objects. The shape or configuration of the scent device 10 can provide an aesthetic pleasing appearance. For example, the shape and appearance of the scent device can differ significantly from traditional air fresheners. Other air fresheners often have a utilitarian appearance, such as cans or canisters, while others have an appearance associated with air fresheners. Thus, the air freshener 10 of the present invention can have a shape and appearance not typically associated with air fresheners. For example, the air freshener 10 can have a substantial appearance and shape of an insect or bug, as shown. Various surface treatments, such as the ribs or slots, can add to the appearance, such as by adding strips, etc. In addition, the air freshener or carrier material can have a color that adds to the appearance. It will be appreciated that other shapes or appearances are possible. For example, the air freshener can be configured to blend in with the environment in which it is used. For example, the scent device can be shaped and configured to appear as a button to blend in with a dashboard. Alternatively, the air freshener can be shaped, sized and colored to stand out, and act as a promotional device or advertisement. For example, the air freshener can be shaped as a logo of an automobile manufacturer.

Figure 16:
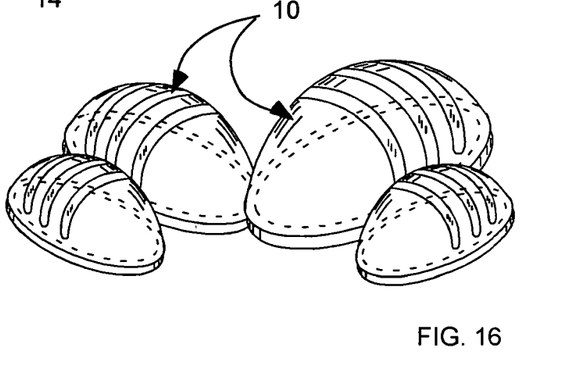
FIG. 16 is a perspective view of a plurality of air fresheners in accordance with an embodiment of the present invention.
Figure 17:
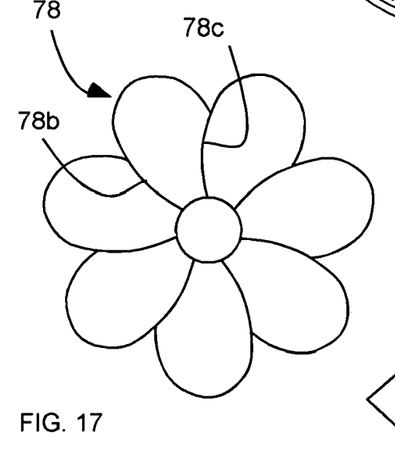
FIG. 17 is a top view of a plurality of air fresheners in accordance with an embodiment of the present invention.

In addition, one or more air fresheners can be, provided as collectables. For example, the air freshener can be shaped, configured or printed to indicate a commemorative event, such as a business anniversary, a holiday, etc. As another example, a plurality of different air fresheners can be provided in families or groups, with each air freshener having a different size, shape, and/or color, as shown in FIG. 16. As another example, a plurality of different air fresheners can be provided with different shapes that fit together or coordinate to form another object, such as a flower, etc, as shown in FIG. 17. The air fresheners 78 can include mating protrusions 78*b* and recesses 78*c*, so that the air fresheners can be fitted together to form another object or design.

As described above, various indicia can be provided with the air freshener. Such indicia can be molded or printed on the top of the air freshener or on the scent portion. The scent portion or gel can be translucent or transparent, and indicia can be provided on the barrier, or on the top surface of the pad. Thus, the indicia is visible through the scent portion or gel. The air freshener can be placed, such as on a windshield, such that the scent material or gel appears to light or glow when light shines through it. The pad and barrier can also be translucent or transparent so that the entire air freshener can be translucent or transparent, and so light can shine through the entire air freshener. As described above, the barrier 58 or other reflective material can be disposed behind or beneath the scent portion or gel to reflect light.

In addition, a phosphorescent material can be provided in the base or the scent portion so that the air freshener, or portion thereof, lumineses or glows. In addition, the indicia can include a phosphorescent material. Furthermore, another material can be added to the scent portion or gel that causes the scent portion or gel to change colors due to changes in temperature or light. For example, the scent portion or gel can be one color in the sunlight, and another color in shadows or darker conditions.

In addition, the air freshener can include an end-of-life indicator when it is time to replace the air freshener. The useful life of the scent device can vary, and can be a typical period, such as 30 days. For example, the air freshener or scent portion can include a material that changes color or other characteristic over time. For example, the air freshener or scent portion can change from translucent or clear to opaque. Alternatively, the air freshener or scent portion can change from opaque to translucent or clear. Indicia, such as "time to replace," may be provided under the scent portion so that the indicia becomes visible over time. Alternatively, the air freshener or scent portion can change from one color to another.

In addition, the air freshener can be sized to conform to non-chocking requirements, and can be formed from non-toxic materials. Furthermore, the air freshener or portion thereof can include a material that is bitter to the taste to discourage individuals from placing the device in their mouths.

Figure 8:
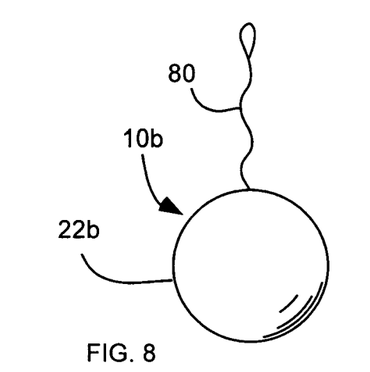
FIG. 8 is a side view of an air freshener is accordance with an embodiment of the present invention.

Referring to FIG. 8, another scent device or air freshener 10*b* is shown that is similar in many respects to that described above. The air freshener 10*b* includes a carrier material 22*b* similar to that described above, such as a polymer body or a polymer gel with a scented oil therein. The air freshener 10*b* can also include a hanger 80, such as a string, wire, clip, etc. from which to suspend or hang the carrier material 22*b* or polymer gel. As described above, it has been found that the polyurethane gel is capable of substantially maintaining its form. In addition, it has been found that the scented oil surprisingly does not leak from the polymer gel and/or stain surfaces. Thus, the air freshener 10*b* can be suspended or hung as desired.

Figures 9, 10, 11, 12, 13:
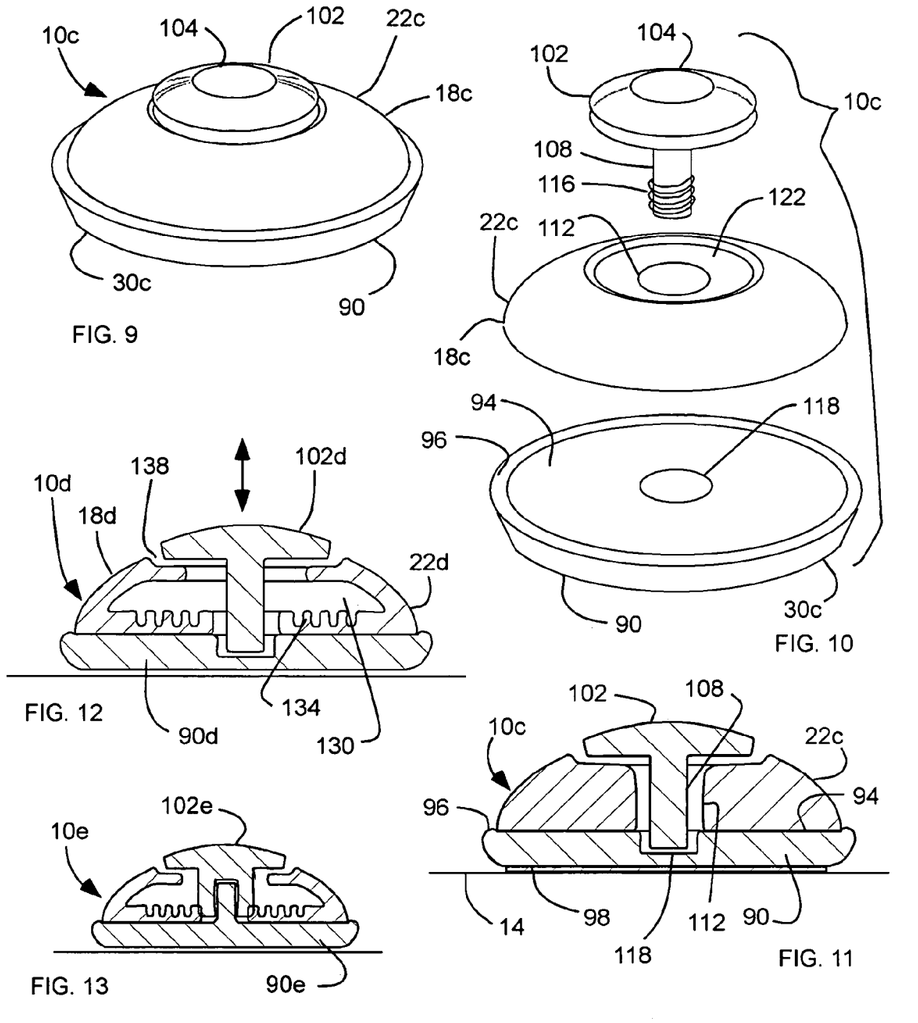
FIG. 9 is a perspective view of an air freshener in accordance with an embodiment of the present invention.
FIG. 10 is an exploded view of the air freshener of FIG. 9.
FIG. 11 is a cross-sectional side view of the air freshener of FIG. 9.
FIG. 12 is a cross-sectional side view of an air freshener in accordance with an embodiment of the present invention.
FIG. 13 is a cross-sectional side view of an air freshener in accordance with an embodiment of the present invention.

Referring to FIGS. 9-11, another scent device or air freshener 10*c* is shown that is similar in many respects to those described above. The air freshener 10*c* can include a scent portion 18*c* disposed on an attachment portion, grip portion or base 30*c*. The scent portion 18*c* can include a carrier material 22*c*, similar to those described above, and the base 30*c* can include a tray 90. The carrier material 22*c* can be similar to that described above, a polyurethane gel with a scented oil.

Alternatively, the carrier material can include a scented plaster. The tray 90 can include a depression or indentation 94 therein formed by a perimeter lip 96 extending around the tray. The tray 90 can be formed of nylon, and can act as a barrier between the scented portion 18*c* or carrier material 22*c* and the surface 14. An attachment means can be disposed on the bottom of the tray 90 to attach or secure the tray to the surface 14. The attachment means can include a polyurethane material 98 to frictionally grip the surface 14, as described above. Other attachment means can be used, including for example, adhesive, tape, hook-and-loop type fasteners, etc.

A button 102 can be utilized to secure the scent portion 18*c* or carrier material 22*c* to the tray 90 and/or to provide a visible surface 104. The visible surface 104 can be formed in the proximal end of the shaft and can be formed on an enlarged head capable of receiving indicia thereon. The indicia can include logos, advertisements, instructions, warnings, etc.

The button 102 can include a shaft 108 that extends through a bore or hole 112 in the scent portion 18*c* or carrier material 22*c*. A distal end 116 of the shaft 108 can be secured to the tray 90, such as in an indentation 118, in any appropriate manner, including sonic welding, press fit, mating screw threads, snap fit, etc. The button 102 can permanently or temporarily secure the scent portion 18*c* or carrier material 22*c*. The entire air freshener can be disposable, or the scent portion 18*c* can be removed and replaced.

The air freshener can be round or oblong, and can have a partially bulbous shape, or a partially spherical shape. The scent portion 18*c* or carrier material 22*c* can include an indentation or recess 122 to receive the button 102 or head thereof. Thus, the button or head can be flush or substantially flush with the scent portion 18*c*.

Referring to FIG. 12, another air freshener 10*d* is shown that is similar in many respects to those described above. The air freshener 10*d* can be configured to maximize or control the amount of scent dispersed. The scent portion 18*d* or carrier material 22*d* can have a hollow interior or cavity 130 with an interior surface to maximize the surface area of the scent portion 18*d* or carrier material 22*d*, and thus the amount of scent released. In addition, interior ribs or fins 134, and/or grooves or channels, can be formed in the scent portion 18*d* or carrier material 22*d*. A gap 138 can be formed between the scent portion 18*d* and the head of the button 102*d*. The gap 138 can extend to the cavity 130. Thus, the scent from the hollow interior can be released through the gap.

The button 102*d* can be adjustably coupled to the tray 90*d*, and selectively movable with respect to the tray. For example, the button 102*d* can be coupled to the tray 90*d* by mating screw threads. Alternatively, the button 102*d* can snap between two or more positions. Thus, the button 102*d* can be selectively positioned with respect to the tray, and the size of the gap 138 can be selectively adjusted, to selectively control the amount of scent released.

Referring to FIG. 13, another air freshener 10*e* is shown that is similar in many respects to those described above. The tray 90*e* can include a protrusion extending into a cavity on the button 102*e*.

Figure 14:
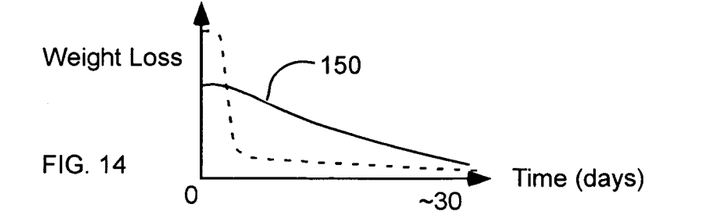
FIG. 14 is a schematic representation of a graph of scent release over time of an air freshener in accordance with an embodiment of the present invention.

Referring to FIG. 14, the carrier material or polymer gel of the present invention can disperse at a substantially constant rate, or can have a substantially constant or linear scent release over time. The scent release can be determined by measuring the weight of the device over time. As scent is released, the scent material disperses out of the carrier material, reducing the weight of the carrier material. As shown in FIG. 14, the scent release or weight reduction can extend substantially linearly over time, represented by solid line 150. The carrier material and scent can be formulated to release a substantial amount of the scent material in a predetermined time period, such as between 2 to 30 days. The dashed line represents typical prior art air fresheners that quickly release scent.

Figure 18:
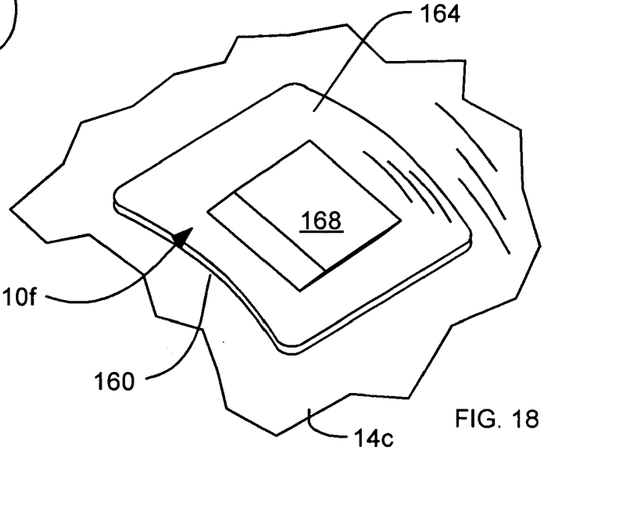
FIG. 18 is a perspective view of another air freshener in accordance with an embodiment of the present invention.

Referring to FIG. 18, another air freshener 10*f* is shown that is similar in many respects to those described above. The air freshener 10*f* can be shaped and sized, or the carrier material 22*f* or gel can be formulated, to be substantially flexible or bendable. For example, the air freshener can be relatively thin, and can readily conform to a surface 14*c* that also can be curved. Thus, the air freshener can have a thin polymer body. The thin polymer body can be flexible and conformable, but resilient and returnable to its original configuration. The air freshener 10*f* or carrier material 22*f* can have an attachment surface 160 for attachment to a surface, such as glass. The attachment surface 160 can be tacky or clingy so that it can cling to the surface without chemical adhesives or mechanical fasteners, as described above. Thus, the air freshener 10*f* can be a simple device capable of being removably secured to a surface, such as a windshield or mirror. In addition, the air freshener 10*f* can include a support surface 164 configured to hold or support another object 168, similar to that described above. The support surface 164 can also be tacky or clingy to cling to the other object.

Figure 19:
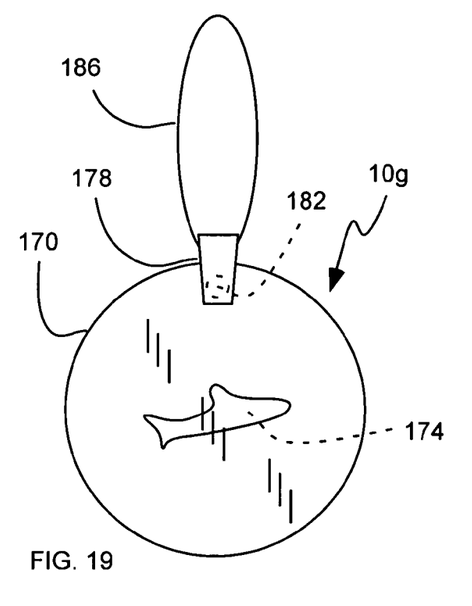
FIG. 19 is a front view of another air freshener in accordance with an embodiment of the present invention.
Figure 20A:
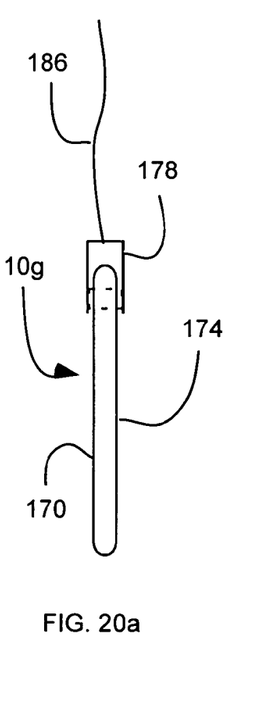
FIG. 20a is a side view of the air freshener of FIG. 19.
Figure 20B:
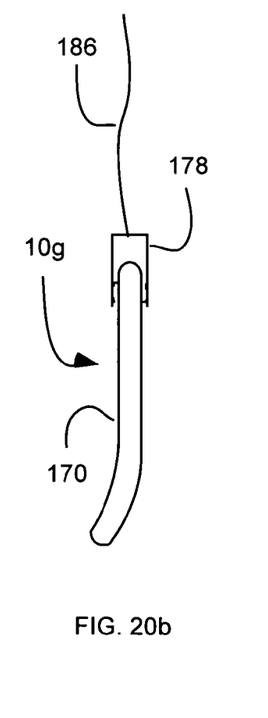
FIG. 20b is a side view of the air freshener of FIG. 19, shown in a deflected configuration.
Figure 20C:
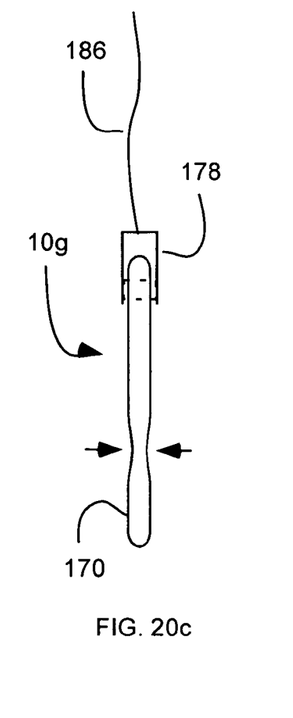
FIG. 20c is a side view of the air freshener of FIG. 19, shown is a compressed configuration.

Referring to FIGS. 19-20*c*, another scent device or air freshener 10*g* is shown that is similar in many respects to those described above. The air freshener 10*g* includes a polymer body or carrier material 170 similar to that described above, such as a polymer body or a polymer gel or thermoplastic elastomer with a scented oil therein. The carrier material 170 can be shaped so that it is relatively thin, or having a thickness less than a width and a height. The carrier material 170 can be light transparent in at least a translucent manner. Indicia 174, such as figures, text, logos, etc., can be disposed on a surface of the carrier material 170, and visible through the carrier material, such as at an opposite side of the carrier material. The indicia 174 can be printed on the surface of the carrier material 170. Thus, the translucent and transparent carrier material and indicia can provide a unique optical appearance. The carrier material can be substantially transparent so that the indicia is clearly visible. The carrier material can be translucent, and can include a color, to modify the light passing through the carrier material. Similarly, the indicia can be translucent so that both the carrier material and the indicia modify the light.

In addition, the carrier material 170 can be flexible. The flexibility can be provided by the material and/or the size or thickness of the carrier material. Thus, the carrier material 170 can be deflected or bent, as shown in FIG. 20*b*. Bending the carrier material can also add a unique optical appearance. In addition, bending the carrier material can mix or displace the scented oil in the carrier material, to increase scent release. Furthermore, the carrier material 170 can be compressible, as shown in FIG. 20*c*. Compressing the carrier material can add a unique optical appearance, and can mix or displace the scented oil to increase scent release. The carrier material can be resilient or elastic, or can maintain is form or return to its original form after deflection or compression.

The air freshener 10*g* can also include a clip 178 that engages the carrier material 170. The clip 178 can include a portion 182 that extents through an aperture in the carrier material. The clip 178 can form a loop to receive a hanger 186, such as a string, wire, strap, etc. from which to suspend or hang the carrier material.

Figure 21:
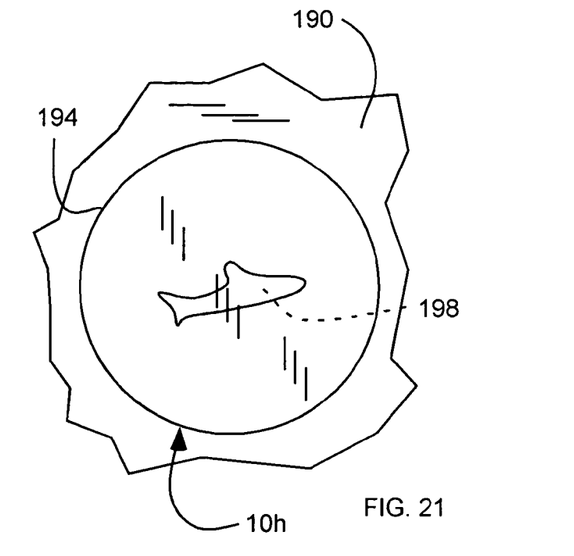
FIG. 21 is a front view of another air freshener in accordance with an embodiment of the present invention shown disposed on a surface.

Referring to FIG. 21, another air freshener 10*h* is shown that is similar in many respects to those described above that clings to a surface, such as a window or windshield 190. The air freshener 10h includes a polymer body or carrier material 194 similar to that described above, such as a polymer body or a polymer gel or thermoplastic elastomer with a scented oil therein. The carrier material 194 can be shaped so that it is relatively thin, or having a thickness less than a width and a height. The carrier material 194 can be light transparent in at least a translucent manner. Indicia 198, such as figures, text, logos, etc., can be disposed on a surface of the carrier material 194, and visible through the carrier material, such as at an opposite side of the carrier material. The indicia 198 can be printed on the surface of the carrier material 194. Thus, the translucent and transparent carrier material and indicia can provide a unique optical appearance. The air freshener 10h or carrier material 194 can have a surface that is tacky or that frictionally clings to the surface. Thus, the air freshener can be releasably secured to a lighted or light transmissive surface, such as an automobile windshield, a home or office window, a mirror, etc. Light passing through the surface will also pass through the carrier material 194. In addition, the indicia can be translucent so that both the carrier material and the indicia can modify light passing therethrough. Thus, the air freshener can have an appearance similar to stained glass or the like.

The air freshener 10h or carrier material 194 can have a surface that is tacky or that frictionally clings to the surface in a releasable manner without modifying or marring the surface as with mechanical or chemical adhesives. Thus, the air freshener 10h can be selectively disposed about the surface as desired, and removed for disposal. The air freshener can have an attachment surface similar to those described above. The indicia can be disposed on the attachment surface, and thus disposed between the carrier material and the window to protect the indicia.

Furthermore, the indicia can be disposed in the air fresheners or carrier materials described above, and visible therethrough. For example, the indicia can be printed on a substrate that is inserted into the carrier material during molding.

The present invention also provides for a method for providing a desired fragrance including securing a tacky attachment surface of a pad of an air freshener to a window, such as a window of a vehicle. The tacky attachment surface can frictionally cling to the window by specific or mechanical adhesion. The air freshener can include a scent material carried by and dispersable through a coherent, elastomeric polymer body that is light transmissive in at least a translucent manner. The pad can be selectively removed from the window. Thus, one or more such air fresheners can be disposed on a window in an aesthetically pleasing manner, such as in a pattern.

Figure 22:
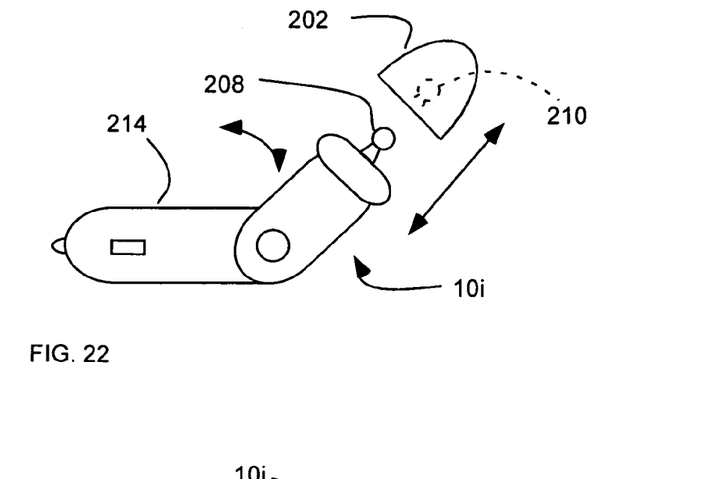
FIG. 22 is a side exploded view of another air freshener in accordance with an embodiment of the present invention.

Referring to FIG. 22, another air freshener 10i is shown that is similar in many respects to those described above and includes a light source that allows the air freshener to illuminate or glow, and that can also provide heat to increase a rate of release of scent from the air freshener. The air freshener 10i includes a polymer body or carrier material 202 similar to that described above, such as a polymer body or a polymer gel or thermoplastic elastomer with a scented oil therein. The carrier material 202 can be shaped so that it is bulbous to provide an aesthetically pleasing design while also increasing an exposed surface area of the material to increase a release rate of scent.

In addition, the carrier material 202 can be light transparent in at least a translucent manner. As described above, indicia (not shown), such as figures, text, logos, etc., can be disposed on a surface of the carrier material 202, and can be visible through the carrier material, such as at an opposite side of the carrier material. The indicia can be printed on the surface of the carrier material. Thus, the translucent and transparent carrier-material and indicia can provide a unique optical appearance. In addition, the indicia can be translucent so that both the carrier material and the indicia can modify light passing therethrough.

A light source 208, such as a light bulb or light emitting diode (LED) can be coupled to or adjacent the body or carrier material 202, and can be capable of emitting light visible through the carrier material 202. A cavity 210 can be formed in the body or carrier material 202 to receive the light source 208 in the cavity 210. Thus, the transparent or translucent nature of the carrier material 202, in combination with the light source 208, can cause the carrier material 202 to illuminate. In addition, the light source 206 can create heat that can increase scent release. It will be appreciated that the light source 208 can be selectively activated to create a unique visual appearance, and/or to increase a rate of release of scent from the carrier material.

The air freshener 10i can include a power source (not shown), such as a battery, to power the light source 208; or can include a power coupling for connecting the freshener to a power source. For example, the air freshener 10i can include a vehicle accessory, or cigarette lighter, power plug 214 that is sized and shaped to be inserted into a vehicle accessory, or cigarette lighter, power socket. Thus, the air freshener can be disposed in, and operated within, a vehicle and can be powered by a power source already present in most modern vehicles. The vehicle accessory power plug 214 can include an articulated, pivoted, or flexible arm to allow the light source 208 and carrier material or body 202 to be selectively positioned or directed. It will be appreciated that vehicle accessory power sockets can have different orientations and positions. Thus, the arm can allow desired positioning of the light source or body.

The body or carrier material 202 can be removably disposed on the power source or plug 214 and light source 208. Thus, the body or carrier material 202 can be selectively removed and replaced to provide different smells, colors, etc. to the interior of the vehicle. In addition, the body or carrier material can be easily replaced when depleted without requiring that the entire unit be replaced.

Figure 23A:
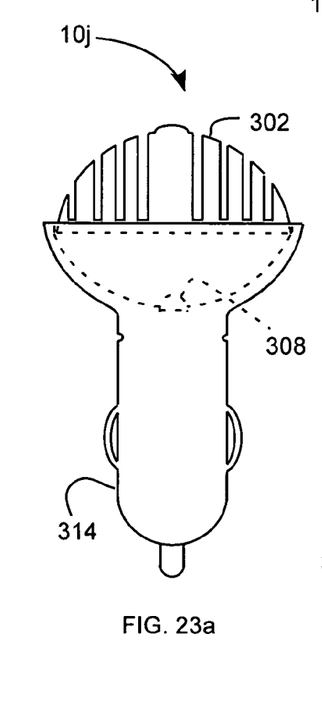
FIG. 23a is a front view of another air freshener in accordance with an embodiment of the present invention.
Figure 23B:
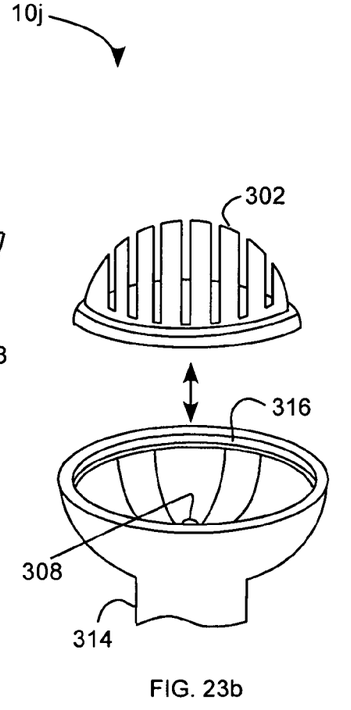
Figure 23C:
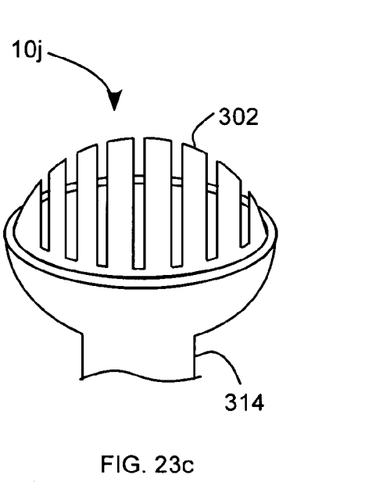

Referring to FIGS. 23a-23c, another air freshener 10j is shown that is similar in many respects to those described above and includes a light source that allows the air freshener to illuminate or glow. The air freshener 10j includes a polymer body or carrier material 302 similar to that described above, such as a polymer body or a polymer gel or thermoplastic elastomer with a scented oil therein. The carrier material 302 can be shaped so that it is bulbous to provide an aesthetically pleasing design while also increasing an exposed surface area of the material to increase a release rate of scent. In addition, the carrier material 302 can be light transparent in at least a translucent manner, and can include indicia that is also transparent or translucent so that both the carrier material and the indicia can modify light passing therethrough.

A light source 308, such as a light bulb or light emitting diode (LED) can be coupled to or adjacent the body or carrier material 302, and can be capable of emitting light visible through the carrier material 302. As noted above, the light source 308 can be selectively activated to create a unique visual appearance, and/or to increase a rate of release of scent from the carrier material.

The air freshener 10j can include a power source (not shown), such as a battery, to power the light source 308; or can include a power coupling for connecting the freshener to a power source. For example, the air freshener 10j can include a vehicle accessory power plug 314 that is sized and shaped to be inserted into a vehicle accessory power socket, such as a cigarette lighter. In one aspect, the vehicle accessory power plug 314 can include an articulated, pivoted, or flexible arm to allow the light source 308 and carrier material or body 302 to be selectively positioned or directed. In another aspect, the vehicle accessory power plug 314 is rigid and merely positions the carrier material near the vehicle accessory power socket.

The body or carrier material 302 can be removably disposed on the power source or plug 314 and light source 308. Thus, the body or carrier material 302 can be selectively removed and replaced to provide different smells, colors, etc. to the interior of the vehicle. In addition, the body or carrier material can be easily replaced when depleted without requiring that the entire unit be replaced.

The air freshener 10j can also include a receptacle 316 sized and shaped to receive at least a portion of the carrier material body 302 adjacent the light source. The carrier material 302 can be removably disposed in the receptacle 316. The air freshener can include a pad as described above, and can frictionally cling to the receptacle 316 by specific or mechanical adhesion.

Figure 24A:
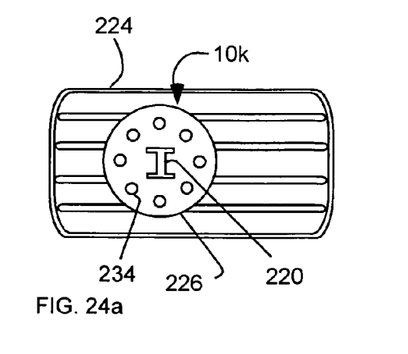
FIG. 24a is a front view of another air freshener in accordance with an embodiment of the present invention shown coupled to an air vent of a vehicle.
Figure 24B:
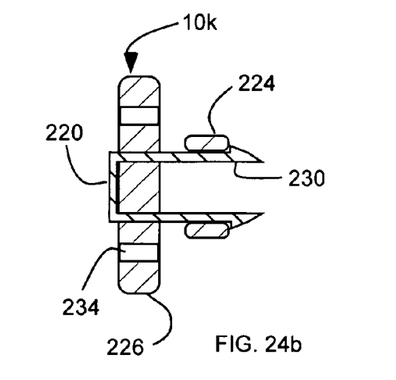

Referring to FIGS. 24a and 24b, another air freshener 10k is shown that is similar in many respects to those described above and includes a clip 220 that can allow the air freshener to be secured to an air vent 224, such as on a vehicle. As described above, the air freshener 10j includes a polymer body or carrier material 226, such as a polymer body or a polymer gel or thermoplastic elastomer with a scented oil therein. Positioning the air freshener 10k in front of an air vent can increase scent dispersal as air blows through the vent and through or around the polymer body. In addition, if the air being blown through the vent is warm, the rate of scent dispersal from the carrier material can be increased. The clip 220 can be coupled to the body or carrier material 226 and can have one or more projections or prongs 230 that extend from the clip and body to engage the air vent 224. Such air vents 224 typically include a grid or array of spaced apart ribs. The projections or prongs 230 can extend into the grid or array of ribs, and can have barbs to engage the grid or ribs. A web can extend between the projections or prongs to connect the prongs, and the projections or prongs can extend through the body or carrier material to couple the clip to the body or carrier material.

The body or carrier material 226 can include a plurality of holes 234 extending through the body to increase the exposed surface area of the carrier material, and thus increase the rate at which the scent is released.

Figures 25, 26, 27A, 27B:
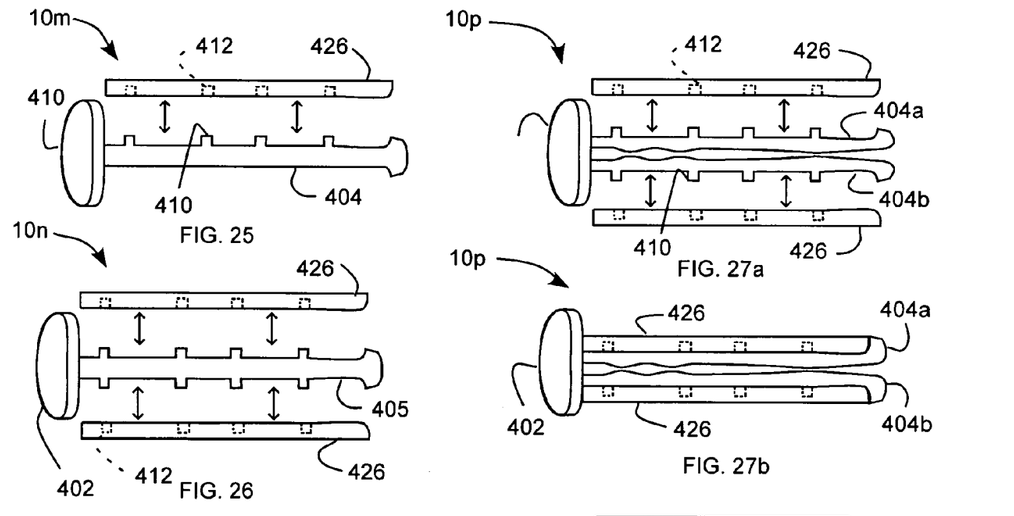

Referring to FIG. 25, another air freshener 10m is shown that is similar in many respects to those described above and includes a head 402. The head 402 can have indicia as describe above. The air freshener 10m can also include a vent rod 404 that can be coupled to and extend away from the head 402. The rod 404 can be sized and shaped to be inserted into an air vent 224 (FIG. 24a), such as on a vehicle, to allow the air freshener to be secured in the air vent 224. As described above, the air freshener 10j also includes a polymer body or carrier material 426, such as a polymer body or a polymer gel or thermoplastic elastomer with a scented oil therein.

The carrier material 426 can have a size and shape similar to the size and shape of the rod 404. The carrier material 426 can be coupled to the rod 404 and extend into the vent 224 with the rod. In one aspect, the rod 404 can have a plurality of protrusions 410 spaced at predetermined intervals along the rod, and the carrier material 426 can have a plurality of apertures 412 corresponding to the protrusions 410 on the rod 404. The carrier material 426 can be coupled to the rod 404 by snapping the apertures 412 onto the protrusions 410. In this way, the carrier material 426 can be inserted with the rod into the air vent to increase scent dispersal as air blows through the vent and through or around the polymer body.

Referring to FIG. 26, another air freshener 10n is shown similar in many respects to the air freshener 10m described above. The air freshener 10n can have plurality of protrusions 410 on a top side 414 and a bottom side 416 of the vent rod 405. In this way, a carrier material 426 can be coupled to the top 414 of the rod 405 and another carrier material 426 can be coupled to the bottom 416 of the rod 405, or separate carrier materials can be disposed on opposite sides of the rod.

Figure 27C:
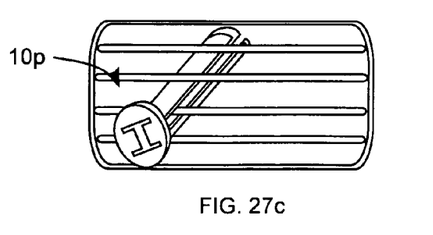
FIG. 27c is a perspective view of the air freshener of FIG. 27a shown coupled to an air vent of a vehicle.

Referring to FIG. 27a-27c, another air freshener 10p is shown that is similar in many respects to those described above. The air freshener 10p can have a head 402 and can include a pair of rods 404a and 404b. The pair of rods 404a and 404b can form a clip that can be sized and shaped to be inserted into the vehicle air vent. The pair of rods 404a and 404b can clip around a vane 430 on a vehicle air vent cover 432. Additionally, each rod 404a and 404b can carry a carrier material 426.

Figure 28A:
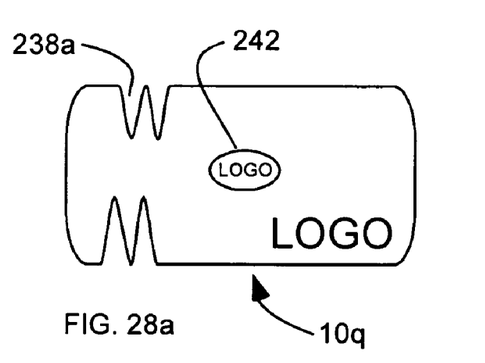
FIGS. 28a and 28b are front views of air fresheners in accordance with embodiments of the present invention.
Figure 28B:
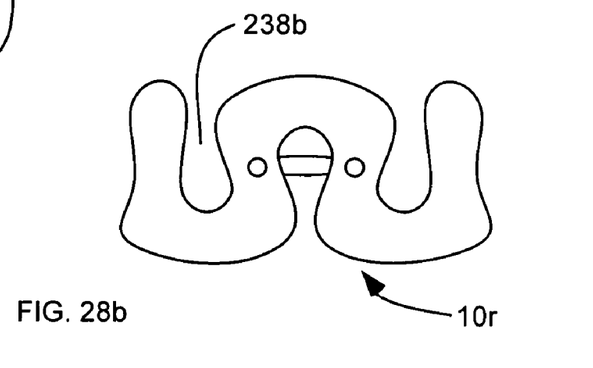

Referring to FIGS. 28a and 28b, air fresheners 10q and r, respectively, are shown with bodies or carrier materials having shapes which can maximize exposed surface area of the freshener. Such shapes can include slots or indentations 238a and 238b. In addition, the air fresheners can include indicia, such as logos, disposed on the body or carrier and/or the clip 242, as shown in FIG. 24a.

Figure 29:
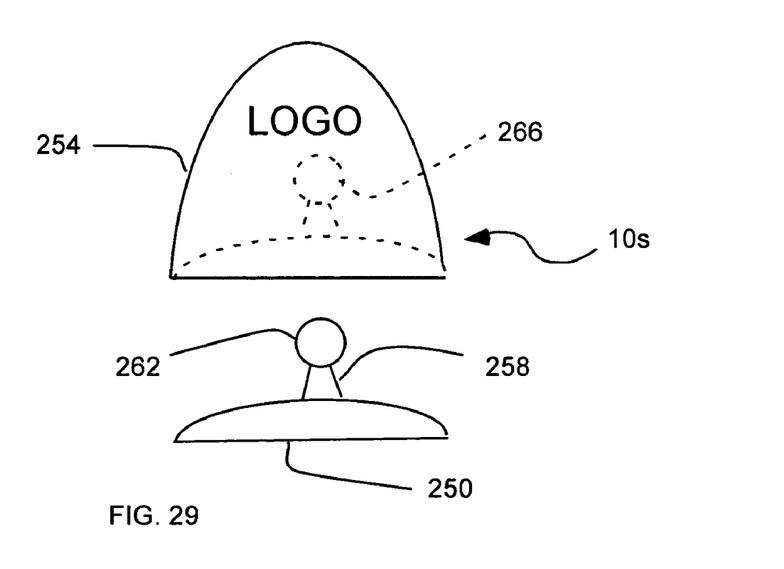
FIG. 29 is an exploded side view of another air freshener in accordance with an embodiment of the present invention.

Referring to FIG. 29, another air freshener 10s is shown that is similar in many respects to those described above, and can include a suction cup 250 to secure the body or carrier material 254 to a surface. As described above, the air freshener 10s includes a polymer body or carrier material 226, such as a polymer body or a polymer gel or thermoplastic elastomer with a scented oil therein. The suction cup 250 can be coupled to the body or carrier material 226 in a variety of manners, as would occur to one skilled in the art. In the embodiment shown, a projection 258 can extend from the suction cup, and can have an enlarged head 262. The body or carrier material 254 can have a cavity 266 with a corresponding enlargement to receive the enlarged head of the projection to couple the body to the suction cup. The body can be resilient and flexible to allow the body to expand over the enlarged head so that the body can be selectively removed and coupled to the suction cup.

Figure 30:
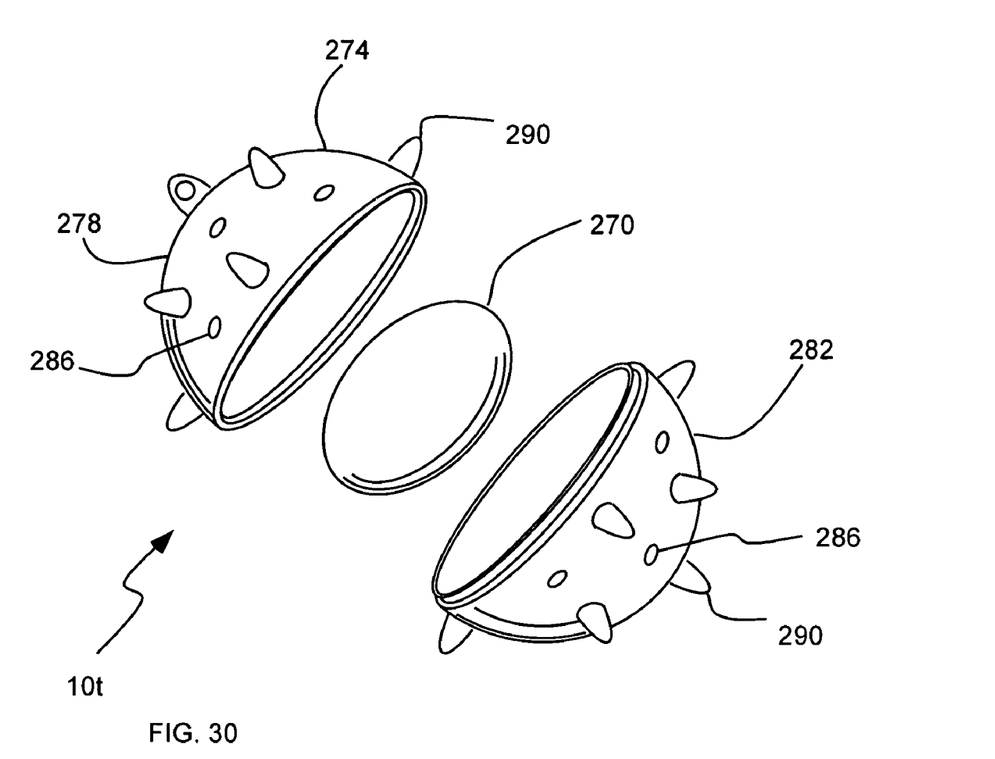
FIG. 30 is an exploded perspective view of another air freshener in accordance with an embodiment of the present invention.

Referring to FIG. 30, another air freshener 10t is shown that is similar in many respects to those described above, and can include an enclosure to allow the air freshener to be placed into close contact with other objects, such as clothes, etc. As described above, the air freshener 10t includes a polymer body or carrier material 270, such as a polymer body or a polymer gel or thermoplastic elastomer with a scented oil therein. The air freshener includes a shell 274 with a hollow or cavity. The body or carrier material 270 can be disposed in the shell within the hollow or cavity. The shell 274 can include a pair of halves 278 and 282 that can be releasably joined together. Thus, the body 270 can be selectively disposed in and removed from the shell. A plurality of holes 286 can be formed through the shell to allow the scent to escape from the shell. In addition, the shell can include a plurality of spines or projections 290 that extend radially outwardly from the shell. The spines can aid in retaining the shell from contacting other objects, such as clothes in a drawer, and can create air pockets between the spines and over the holes to allow the scent to escape. The shell or enclosure can include attachment means to allow the enclosure to be suspended from a hanger, such as a string or cable.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. An air freshener device, comprising:
   a) a head with indicia;
   b) a clip coupled to the head extending perpendicularly outward from the head, and sized and shaped to be inserted into a vehicle air vent and clipped to a vehicle air vent cover such that the head is adjacent the vehicle air vent, and including a pair of vent rods sized and shaped to be inserted into the vehicle air vent and having a plurality of protrusions;
   c) a pair of coherent elastomeric polymer bodies having a plurality of apertures, each of the bodies coupled to a different one of the vent rods via coupling of the plurality of apertures with the plurality of protrusions, and insertable into the vehicle air vent with the vent rods; and
   d) a scent material, interspersed within the bodies, capable of diffusing out of the bodies to surrounding air.

2. A device in accordance with claim 1, wherein the elastomeric polymer is selected from the group consisting of polyurethane, polyacrylate, polybutadiene, ethylene propylene elastomer, silicone, natural rubber, synthetic rubber, styrene/butadiene block copolymer, polyvinylchloride, ethylene vinyl acetate, polypropylene, ethylene/methacrylic acid copolymer, and mixtures thereof.

3. A device in accordance with claim 2, wherein the elastomeric polymer is selected from the group consisting of polyurethane, polyurethane gel, polyacrylate, polybutadiene, ethylene propylene elastomer, styrene/butadiene block copolymer, and mixtures thereof.

4. A device in accordance with claim 1, wherein the elastomeric polymer is a thermoplastic elastomer.

5. A device in accordance with claim 4, wherein the thermoplastic elastomer is selected from the group consisting of polyurethanes, polyamides, copolyesters, styrene-butadiene-styrene polymers, elastomer/thermoplastic blends, and combinations thereof.

6. A device in accordance with claim 1, wherein the polymer bodies include polyurethane and the scent material includes a scented oil.

7. A device in accordance with claim 1, wherein the polymer bodies are a polymerization product of at least a diisocyanate prepolymer and a scented oil.

8. A device in accordance with claim 7, wherein the polymer bodies and scent material include a polymerization product of:
   a) a polyether polyol;
   b) a diphenylmethane diisocyanate (MDI) prepolymer; and
   c) a scented oil.

9. A device in accordance with claim 1, wherein the scent material in the polymer bodies disperses at a substantially constant rate for at least a time period of between approximately two days and thirty days.

10. A device in accordance with claim 1, wherein the polymer bodies includes a polymeric material with a glass transition temperature greater than approximately 110° F.

11. A device in accordance with claim 1, wherein the elastomeric polymer includes a polyurethane gel.

12. A device in accordance with claim 1, wherein the elastomeric polymer is selected from the group consisting of polyurethane, polyacrylate, polybutadiene, ethylene propylene elastomer, styrene/butadiene block copolymer, and mixtures thereof, the elastomeric polymer being a solid material.

* * * * *